(12) United States Patent
Chen

(10) Patent No.: US 6,968,747 B2
(45) Date of Patent: Nov. 29, 2005

(54) DYNAMIC BALANCE-TESTING METHOD FOR A GOLF CLUB SHAFT

(75) Inventor: Chan-Tung Chen, Kaohsiung (TW)

(73) Assignee: Fu Sheng Industrial Co., Ltd., Taipei (TW)

( * ) Notice: Subject to any disclaimer, the term of this patent is extended or adjusted under 35 U.S.C. 154(b) by 106 days.

(21) Appl. No.: 10/670,371

(22) Filed: Sep. 26, 2003

(65) Prior Publication Data

US 2005/0066712 A1    Mar. 31, 2005

(51) Int. Cl.$^7$ .............................................. G01N 3/20
(52) U.S. Cl. ........................................ 73/854; 473/289
(58) Field of Search .......................... 73/849, 853, 854; 473/289

(56) References Cited

U.S. PATENT DOCUMENTS

| | | | |
|---|---|---|---|
| 4,958,834 A | * | 9/1990 | Colbert ........................ 473/289 |
| 5,515,717 A | * | 5/1996 | White ........................ 73/65.03 |
| 5,976,028 A | * | 11/1999 | Ciccarello et al. .......... 473/289 |
| 6,494,109 B2 | * | 12/2002 | Weiss ........................ 73/865.9 |
| 6,526,613 B1 | * | 3/2003 | Penley ....................... 73/65.03 |

* cited by examiner

Primary Examiner—John E. Chapman
(74) Attorney, Agent, or Firm—Birch, Stewart, Kolasch & Birch, LLP

(57) ABSTRACT

A dynamic balance-testing method for a golf club shaft in accordance with the present invention comprises steps of: fixing a first end of a golf club shaft; measuring reacting forces of a constant displacement of a second end of the golf club shaft in a plurality of predetermined angular directions with respect to an axis of the golf club shaft; calculating a minimum difference of reacting force of any two opposite directions; and determining a preferred balance direction according to the minimum difference of reacting force and thus selecting a preferred striking direction perpendicular to the balance direction of the golf club shaft for assembling.

5 Claims, 4 Drawing Sheets

DYNAMIC BALANCE-TESTING METHOD FOR A GOLF CLUB SHAFT

BACKGROUND OF THE INVENTION

1. Field of the Invention

The present invention is related to a dynamic balance-testing method for a golf club shaft. More particularly, the present invention is related to the dynamic balance-testing method to measure a lateral flexibility by static force for determining a preferred striking direction of the golf club shaft.

2. Description of the Related Art

Generally, isotropy quality of a golf club shaft determines a dynamic balance character for striking. The more the golf club shaft has a high character of dynamic balance, the more it accomplishes a striking aspect, such as a striking accuracy and a striking distance. It means that a high character of dynamic balance minimizes a lateral component of force (lateral deformation) and vibration. However, a conventional manufacture method cannot ensure perfect straightness and isotropy of the golf club shaft, particularly a carbon fiber shaft. Accordingly, some non-isotropy of the golf club shaft is inevitable and results in some unbalance of the dynamic balance character. To this end, a golf club shaft must measure its isotropy on a circle with respect to an axis prior to being combined with a golf club head. An operator determines a desired striking direction of the golf club shaft by measuring and searching a minimum lateral component of force. This is regarded as a reference of striking aspect for improvement.

Referring to FIGS. 1, 1A and 1B, a conventional dynamic balance-testing method adopts a measuring manner that shakes a golf club shaft 10 for measuring dynamic balance character. First, an end of the golf club shaft 10 is fixed on a damper 20. Subsequently, a constant force acts on the other end of the golf club shaft 10 along a direction P1, as shown in FIGS, 1 and 1A. Once the force is removed from the golf club shaft 10, the end of the golf club shaft 10 causes a vibration. Frequency of vibration is measured within a predetermined time and movement of the golf club shaft 10 is determined to maintain along a straight-line motion. Second, the golf club shaft 10 is rotated to other directions P2–P12 to process previous measurements, including frequency and straight motion, as shown in FIGS. 1 and 1B. Subsequent to testing, the frequencies and the straight motions of the golf club shaft 10 are analyzed. For example, if the frequency between the two opposite directions P2 and P8 is minimum, a line running from P2 to P8 becomes a minimum lateral component of force and obtains a perfect dynamic balance that may enhance striking aspect.

Although the above-mentioned method is widely used in the industry, it prolongs the process time for testing. In addition, a track of the vibrational movement of the golf club shaft 10 cannot be confined within a single degree of freedom due to its nonisotropy. Accordingly, observing the track of the golf club head 10, it is gradually changed to a rotation from a straightline motion that may result in an error of the observational measure and fail to determine an exact direction of isotropy. Hence, there is a need for an improvement of the dynamic balance-testing method for a golf club shaft.

The present invention intends to provide a dynamic balance-testing method which bends an end of a golf club shaft a constant displacement. The dynamic balance-testing method employs a dynamometer to measure a reacting force acted from the bent end of the golf club shaft. Subsequently, the reacting forces of the golf club shaft are measured in predetermined directions so that a chart of distribution of the reacting force is obtained. Thereby, a minimum difference of the reacting forces on two opposite directions is calculated to obtain a striking direction in such a way to mitigate and overcome the above problem.

SUMMARY OF THE INVENTION

The primary objective of this invention is to provide a dynamic balance-testing method for a golf club shaft, which bends an end of a golf club shaft a constant displacement to measure a reacting force, thereby accurately determining dynamic balance character.

The secondary objective of this invention is to provide the dynamic balance-testing method for a golf club shaft, which bends an end of a golf club shaft a constant displacement to measure reacting force, thereby speeding up the entire process.

The dynamic balance-testing method for a golf club shaft in accordance with the present invention comprises steps of: fixing a first end of a golf club shaft; measuring reacting forces of a constant displacement of a second end of the golf club shaft in a plurality of predetermined angular directions with respect to an axis of the golf club shaft; calculating a minimum difference of reacting force of any two opposite directions; and determining a preferred balance direction according to the minimum difference of reacting force and thus selecting a preferred striking direction perpendicular to the balance direction of the golf club shaft for assembling.

Other objectives, advantages and novel features of the invention will become more apparent from the following detailed description and the accompanying drawings.

Further scope of the applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will now be described in detail with reference to the accompanying drawings, which are given by way of illustration only, and thus are not limitative of the present invention, and wherein.

DETAILED DESCRIPTION OF THE INVENTION

Figure 2:
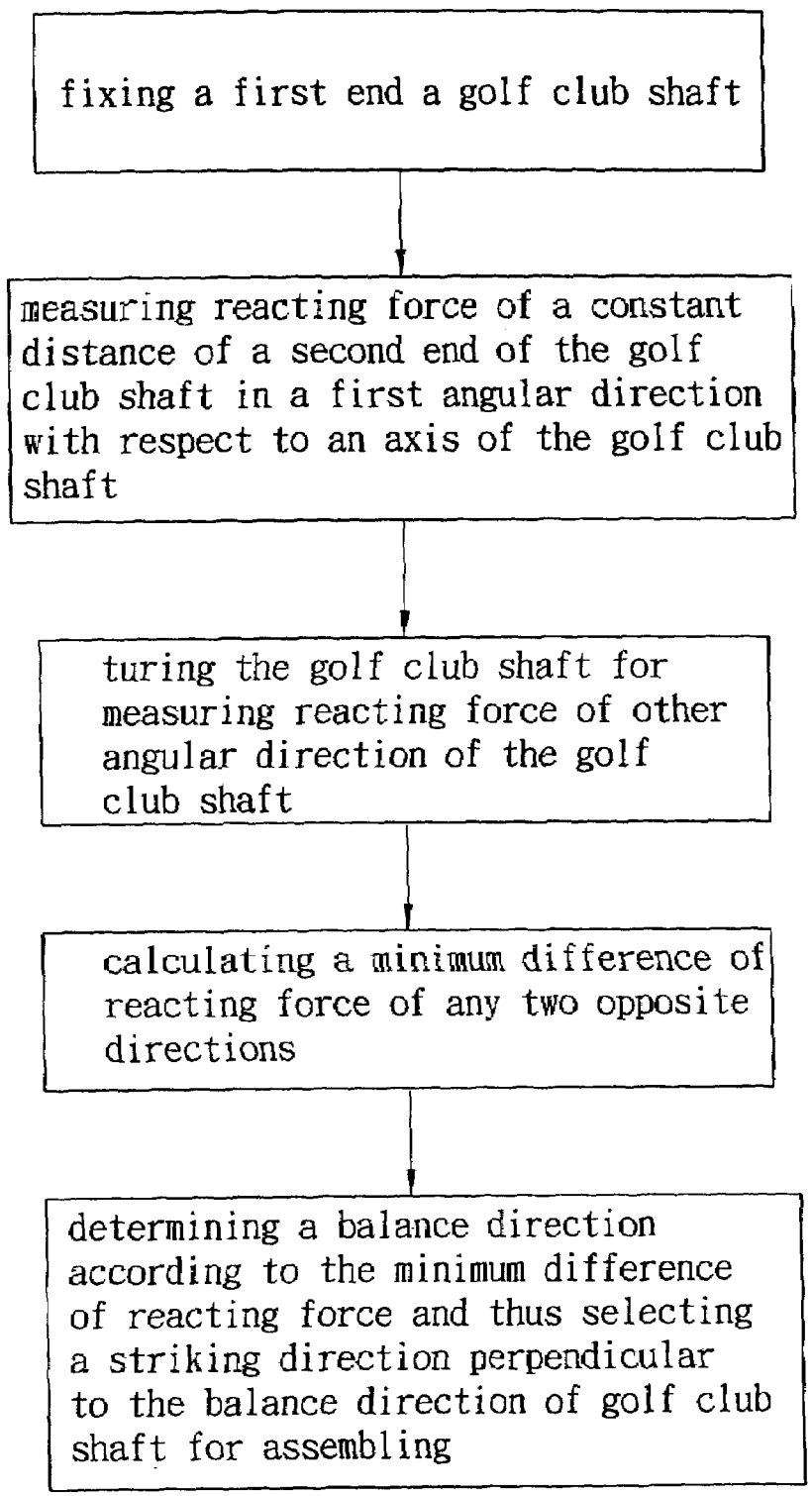
FIG. 2 is a flow chart of a dynamic balance-testing method for a golf club shaft in accordance with the preferred embodiment of the present invention.
Figure 3:
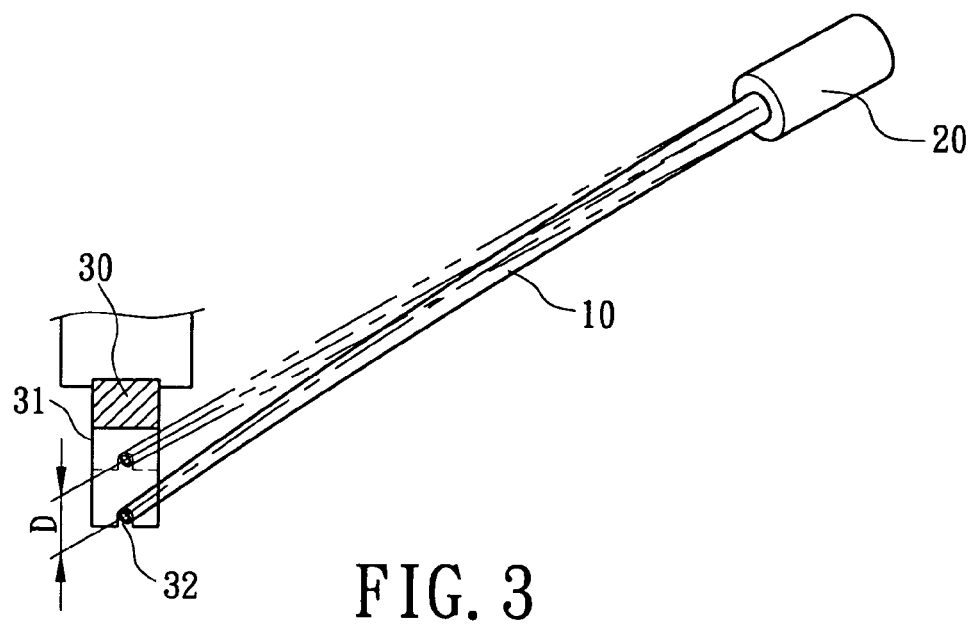
FIG. 3 is a perspective view of the dynamic balance-testing method for a golf club shaft measured by a dynamometer in accordance with the preferred embodiment of the present invention.

Referring initially to FIGS. 2 and 3, a dynamic balance-testing method for a golf club shaft in accordance with the present invention comprises a first step that fixes a first end of a golf club shaft 10. A damper 20 is used to securely mount the first end of the golf club shaft 10 which has a second end. In use, the second end of the golf club shaft 10 has a relatively thin diameter, which is regarded as a striking end to be combined with a golf club head (not shown). The golf club shaft 10 has an axle extended between the first end to the second end in a longitudinal direction, and a radially outer circumference provided with at least twelve predetermined angular directions P1 through P12. Each direction has an opposite direction along a straight line which runs through the axle of the golf club shaft 10, such as P1 corresponding to P7, P2 corresponding to P8. Preferably, a protractor (not shown) is provided on the golf club shaft 10 for accurate axial rotation. In clamping operation, the golf club shaft 10 is able to rotate along its axle for measuring process. Preferably, the damper 20 has an alignment means, such as position marks P1, P2 . . . P12, to determine an exact direction of the predetermined angular directions P1 through P12 of the golf club shaft 10.

Figure 3A:
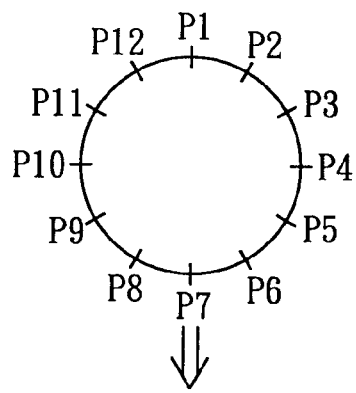
FIG. 3A is a schematic view of reacting force of the golf club shaft, taken along line P1–P7, in accordance with the preferred embodiment of the present invention.

Still referring to FIGS. 2 through 3A, the dynamic balance-testing method for a golf club shaft in accordance with the present invention comprises a second step that measures reacting forces of a constant displacement of the second end of the golf club shaft 10 in the first angular direction P1 with respect to its axis. A dynamometer 30 includes a movable end 31 and a slot 32 thereof. The movable end 31 is able to move a predetermined distance D while the slot 32 holds the second end of the golf club shaft 10, as shown in FIG. 3. In measuring operation, subsequent to the damper 20 fixing the first end of the golf club shaft 10 along the direction P1, the second end of the golf club shaft 10 is rotatably received in the slot 32 of the dynamometer 30. Subsequently, the movable end 31 of the dynamometer 30 forces the second end of the golf club shaft 10 to bend a predetermined constant displacement D, thereby elastically bending the entire golf club shaft 10 along a line running from the direction P1 to the opposite direction P7. Namely, the constant displacement of the golf club shaft 10 can be confined within a single degree of freedom, as shown in FIGS. 3A. When static, the second end of the golf club shaft 10 has a a reacting force acting on the dynamometer 30. Consequently, reacting force data in the direction P1 of the golf club shaft 10 can be retrieved for the calculating process.

Figure 3B:
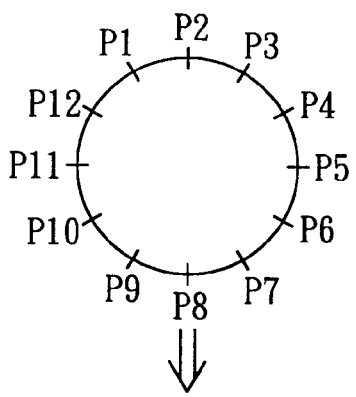
FIG. 3B is a schematic view of reaction force of the golf club shaft, taken along line P2–P8, in accordance with the preferred embodiment of the present invention.

Turning now to FIGS. 3 and 3B, the dynamic balance-testing method for a golf club shaft in accordance with the present invention comprises a third step that turns the golf club shaft 10 for measuring reaction force of the other directions P2–P12 successively by the dynamometer 30. Preferably, the damper 20 is provided with an adjusting member that allows rotation of the golf club shaft 10 and accurately positions it at various directions P1–P12 according to the protractor. Since data of reacting force of the golf club shaft 10 can be automatically collected, it can effectively shorten the measuring process time.

Figure 4:
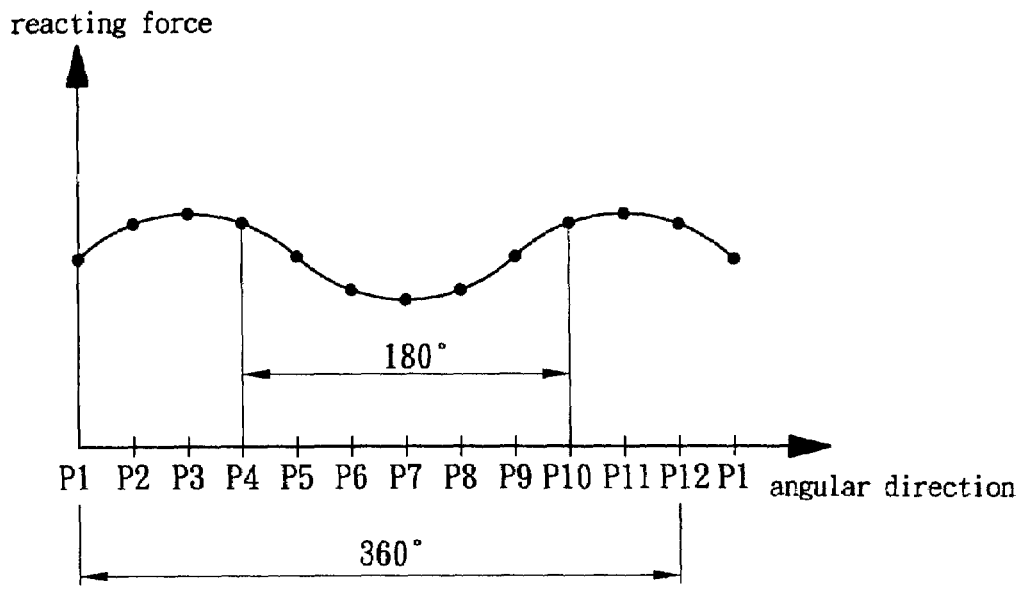
FIG. 4 is a schematic diagram illustrating reacting force of the golf club shaft in relation to angular direction in accordance with the preferred embodiment of the present invention.

Turning now to FIGS. 2 and 4, the dynamic balance-testing method for a golf club shaft in accordance with the present invention comprises a fourth step that calculates a minimum difference of reacting force of any two opposite directions P1–P12. FIG. 4 shows a schematic diagram illustrating a curve of reacting force in relation to directions. In the following step, according to the minimum difference of reacting force, it can thus be determined a preferred balance direction of the golf club shaft 10. As shown in FIG. 4, analyzing data of reacting force of any two opposite directions P1–P12 (such as P1 corresponding to P7, P2 corresponding to P8 . . . P6 corresponding to P12), a calculator can automatically calculate a minimum difference of reacting force and its absolute value. Theoretically, the absolute value of the minimum difference of reacting force is in reverse proportional to dynamic balance character.

Figure 5:
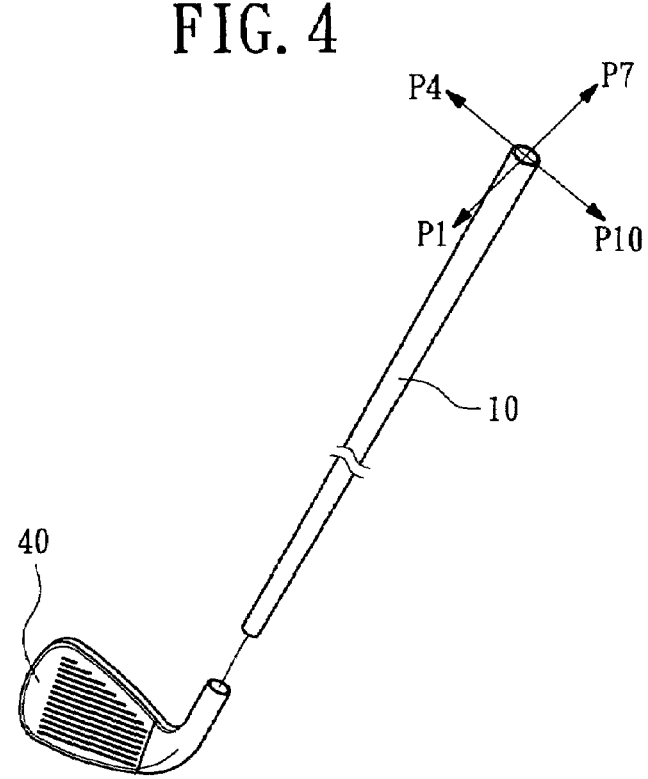
FIG. 5 is a perspective view of the golf club shaft assembled with a golf club head along a desired striking direction in accordance with the preferred embodiment of the present invention.

Turning now to FIGS. 2 and 5, the dynamic balance-testing method for a golf club shaft in accordance with the present invention comprises a fifth step that determines a preferred balance direction according to the minimum difference of reacting force and thus selects a preferred striking direction perpendicular to the balance direction of the golf club shaft 10. If a minimum difference of reacting force is located on a line running from the direction P4 to the opposite direction P10, the isotropy character between the two opposite directions P4 and P10 is excellent. It can be found that a direction along the two opposite directions P4 and P10 is regarded as a preferred balance direction of the golf club shaft 10 for assembling a golf club head 40. Consequently, a preferred striking direction of the golf club shaft 10 is consistent with a line running along the two directions P1 and P7 that is perpendicular to that of the two directions P4 and P10. Namely, when the golf club is swinging along the striking direction of P1 and P7, the isotropy character between the two opposite directions P4 and P10 affects little lateral vibration of the golf club shaft 10. As a result, the golf club shaft 10 has excellent striking aspects such as a striking accuracy and striking distance.

The dynamic balance-testing method for a golf club shaft in accordance with the present invention can employ an automatic control system and an appropriate interface card to control the damper 20 and the dynamometer 30 which may rotate, fix, bend and measure the golf club shaft 10 automatically. Thereby, the present invention accurately determines dynamic balance character and speeds the entire process.

Figure 1:
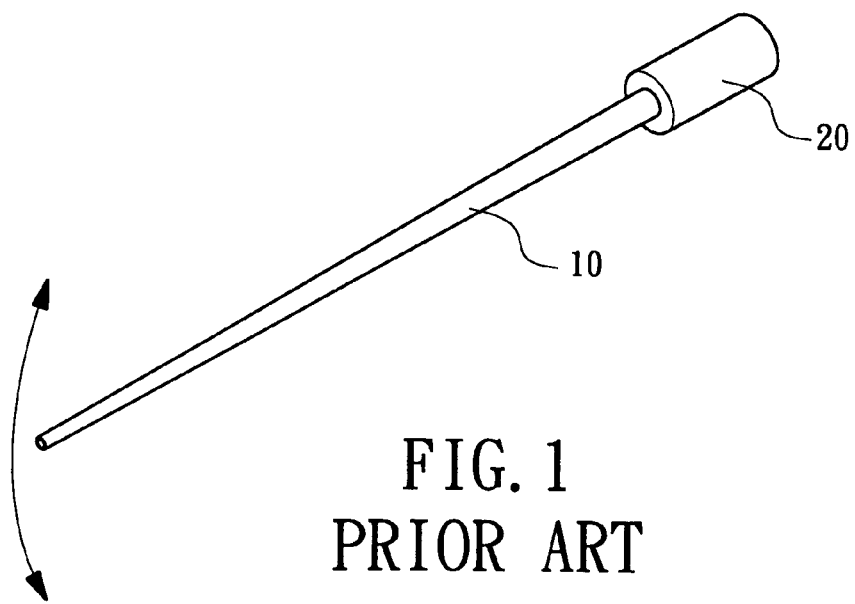
FIG. 1 is a perspective view of a dynamic balance-testing method for measuring a golf club shaft fixed on a damper in accordance with the prior art.
Figure 1A:
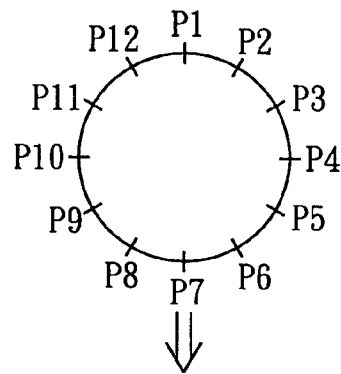
FIG. 1A is a schematic view of vibration of the golf club shaft, taken along line P1–P7, in accordance with the prior art.
Figure 1B:
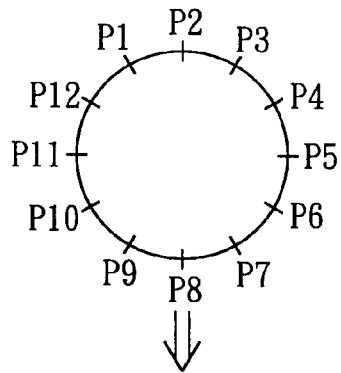
FIG. 1B is a schematic view of vibration of the golf club shaft, taken along line P1–P7, in accordance with the prior art.

Referring again to FIGS. 1 and 3, the conventional dynamic balance-testing method may prolong the process time of testing and fail to determine an exact striking direction of the golf club shaft. In comparison with the conventional method, the present invention employs the dynamometer 30 which accurately determines dynamic balance character and speeds the entire process.

Although the invention has been described in detail with reference to its presently preferred embodiment, it will be understood by one of ordinary skill in the art that various modifications can be made without departing from the spirit and the scope of the invention, as set forth in the appended claims.

What is claimed is:

1. A dynamic balance-testing method, comprising steps of:
    fixing a first end of a golf club shaft, the golf club shaft is provided with a plurality of predetermined angular directions on its radially outer circumference;
    measuring reacting force of a second end of the golf club shaft in the predetermined angular directions with respect to an axis of the golf club shaft;
    calculating a minimum difference of reacting force of any two opposite directions; and
    determined a preferred balance direction according to the minimum difference of reacting force and selecting a preferred striking direction perpendicular to the balance direction of the golf club shaft.

2. The dynamic balance-testing method as defined in claim 1, wherein the first end of the golf club shaft is mounted in a clamper which is rotatable for rotating the golf club shaft and positioning in the predetermined angular directions.

3. The dynamic balance-testing method as defined in claim 1, wherein the reacting force of the second end of the golf club shaft is measured by a dynamometer.

4. The dynamic balance-testing method as defined in claim 3, wherein the dynamometer is formed with a slot adapted to rotatably receive the second end of the golf club shaft.

5. The dynamic balance-testing method as defined in claim 1, wherein the second end of the golf club shaft is bent a constant displacement for measuring the reacting force.

* * * * *